(12) United States Patent
Devlin

(10) Patent No.: US 11,819,395 B2
(45) Date of Patent: Nov. 21, 2023

(54) CONTINUOUS STRIPS OF SANITARY NAPKINS ON A ROLL

(71) Applicant: Egal Pads Inc., Somerville, MA (US)

(72) Inventor: Thomas E. Devlin, Winchester, MA (US)

(73) Assignee: Egal Pads Inc., Somerville, MA (US)

( * ) Notice: Subject to any disclaimer, the term of this patent is extended or adjusted under 35 U.S.C. 154(b) by 633 days.

(21) Appl. No.: 17/012,305

(22) Filed: Sep. 4, 2020

(65) Prior Publication Data

US 2021/0069032 A1   Mar. 11, 2021

Related U.S. Application Data

(60) Provisional application No. 62/896,076, filed on Sep. 5, 2019.

(51) Int. Cl.
*A61F 13/551* (2006.01)
*B65D 75/46* (2006.01)
*A61F 13/56* (2006.01)
*A61F 13/53* (2006.01)

(52) U.S. Cl.
CPC .......... *A61F 13/5514* (2013.01); *B65D 75/46* (2013.01); *A61F 13/53* (2013.01); *A61F 13/5611* (2013.01); *A61F 2013/530481* (2013.01)

(58) Field of Classification Search
CPC .......... A61F 15/00; A61F 2013/530481; A61F 13/5611; A61F 13/53; A61F 13/5514; B65D 75/46
USPC .......................................................... 206/390
See application file for complete search history.

(56) References Cited

U.S. PATENT DOCUMENTS

| | | | | |
|---|---|---|---|---|
| 2,830,910 A * | 4/1958 | Swanson | ................ | B65D 75/46 206/820 |
| 3,131,399 A * | 5/1964 | Murphy | ................ | A41D 13/04 206/390 |
| 3,259,303 A * | 7/1966 | Repko | ................ | B65D 75/5833 383/203 |
| 3,485,349 A * | 12/1969 | Chaney, Jr. | ............ | B65D 75/42 206/820 |
| 3,749,237 A * | 7/1973 | Dorton | ................... | A61B 50/37 206/390 |
| 3,835,992 A * | 9/1974 | Adams, IV | ........ | B65D 83/0835 206/390 |
| 3,851,760 A * | 12/1974 | Smith | ................ | B65D 83/0805 206/390 |
| 3,921,802 A * | 11/1975 | Thompson | ............. | A47K 10/42 206/390 |
| 4,735,342 A * | 4/1988 | Goldstein | ............. | A61F 15/002 206/394 |
| 4,773,532 A * | 9/1988 | Stephenson | ........ | B65D 83/0811 206/390 |
| 4,781,712 A * | 11/1988 | Barabino | ............ | A61F 13/5611 604/385.201 |
| 4,816,320 A * | 3/1989 | St. Cyr | ..................... | B32B 7/02 428/206 |
| 5,484,636 A * | 1/1996 | Berg, Jr. | ............. | A61F 13/5514 604/389 |

(Continued)

*Primary Examiner* — Ernesto A Grano
(74) *Attorney, Agent, or Firm* — Occhiuti & Rohlicek LLP

(57) ABSTRACT

A strip having a weakened region that defines first and second segments on either side thereof. The first and second segments include corresponding first and second sanitary napkins.

20 Claims, 14 Drawing Sheets

(56) References Cited

U.S. PATENT DOCUMENTS

| | | | |
|---|---|---|---|
| 5,569,230 A * | 10/1996 | Fisher | A61F 13/5514 604/389 |
| 5,782,786 A * | 7/1998 | Tomaiuolo | A61F 13/0203 602/41 |
| 5,843,011 A * | 12/1998 | Lucas | A61F 13/023 602/56 |
| 5,971,138 A * | 10/1999 | Soughan | B65D 27/10 206/390 |
| 6,146,365 A * | 11/2000 | Nguyen | B65D 33/002 206/390 |
| 6,425,136 B1 * | 7/2002 | Schlamp | A47L 25/005 206/278 |
| 6,503,326 B1 * | 1/2003 | Mikelionis | A47K 10/32 242/598.5 |
| 6,748,605 B1 * | 6/2004 | Brinkmann | A41D 19/0068 2/167 |
| 7,032,751 B2 * | 4/2006 | Bell | A61B 50/30 206/390 |
| 7,077,073 B2 * | 7/2006 | Judge | A47K 10/16 206/390 |
| 7,093,978 B2 * | 8/2006 | Tan | B31B 70/00 383/120 |
| 7,392,917 B2 * | 7/2008 | Alalu | A47K 10/16 221/48 |
| 7,683,235 B2 * | 3/2010 | Wendorf | A61F 15/001 602/41 |
| 7,811,649 B2 * | 10/2010 | Post | A47L 13/51 206/820 |
| D633,213 S * | 2/2011 | Cowles | D24/189 |
| 7,931,170 B2 * | 4/2011 | Che | B65H 35/10 206/390 |
| D637,299 S * | 5/2011 | Cowles | D24/189 |
| 8,231,590 B2 * | 7/2012 | Zander | A61F 13/84 604/385.03 |
| 8,851,284 B2 * | 10/2014 | Arefieg | B65D 27/00 206/390 |
| D741,406 S * | 10/2015 | Doucette | D19/69 |
| 9,540,144 B2 * | 1/2017 | Tseng | B65D 33/007 |
| 10,293,986 B2 * | 5/2019 | Pitts | B65D 75/566 |
| 10,737,874 B2 * | 8/2020 | Pourian | B65D 83/04 |
| 2001/0042696 A1 * | 11/2001 | Fellinger | B65D 75/327 206/390 |
| 2002/0020648 A1 * | 2/2002 | Lam | B65D 33/002 206/390 |
| 2002/0160896 A1 * | 10/2002 | Yeh | B65D 33/002 206/390 |
| 2003/0045856 A1 * | 3/2003 | Couture | A61F 13/622 604/385.04 |
| 2004/0228990 A1 * | 11/2004 | Hines | B65D 75/42 428/34.1 |
| 2005/0131376 A1 * | 6/2005 | Wheeler | A61F 13/5514 604/386 |
| 2005/0137565 A1 * | 6/2005 | Bryant | A61F 13/5605 604/391 |
| 2007/0179466 A1 * | 8/2007 | Tremblay | A61F 13/5514 604/385.13 |
| 2009/0105680 A1 * | 4/2009 | Amiot | A61F 13/5514 604/385.13 |
| 2013/0248398 A1 * | 9/2013 | Harada | B65B 5/022 206/440 |

* cited by examiner

Section A-A

Alternate Section A-A

Detail B

Section C-C

Section E-E

Alternate Section E-E

Detail F

Section I-I

Section J-J

Alternate Section J-J

Section L-L

CONTINUOUS STRIPS OF SANITARY NAPKINS ON A ROLL

RELATED APPLICATIONS

This application claims the benefit of the priority date of U.S. Provisional Application 62/896,076, which was filed on Sep. 5, 2019, the contents of which are herein incorporated by reference.

FIELD OF INVENTION

This invention relates to sanitary napkins for public use.

BACKGROUND

Menstruating women need to carry sanitary napkins with them at all times in case their menstrual cycles begin when not expected. These are generally discreet packets that can be carried in a purse. A woman often discovers the need for a sanitary napkin while using the toilet. If she is in a stall in a public restroom and she doesn't have a sanitary napkin, she faces a very inconvenient and potentially embarrassing predicament.

A public restroom may have tampons and pads for sale in a vending machine just in case, but a woman would still have to dress and exit the stall to retrieve the product, and she would need to have proper change.

In recent years, the #MeToo movement and women's rights have focused on inequality across society, even in the bathroom. Men do not have to carry toilet paper around because they know that it will be provided in the toilet stall. In the same manner, why can't women have their needs met in the stall?

To satisfy this call for equity, municipalities, restaurants, and businesses are beginning to provide feminine napkins free of charge. This presents challenges in regard to the expense of the product, the need for specialized containers to dispense individual napkins, and the very real potential for customers to steal the product. There is nothing available that addresses these issues.

All products on the market and prior art in this area focus on features such as shape, formulation, or folding and packaging of an individual feminine napkin.

SUMMARY

This invention offers a way to provide sanitary napkins on a roll in much the same manner that toilet paper is provided. A properly executed roll of sanitary napkins would not require a special dispenser and could hang right next to the toilet paper in the stall.

But it is not obvious how to provide this roll. Good product features and cleanliness are needed for public acceptance. But this has to be balanced with cost so that there is provider acceptance and compliance.

The easier and cheaper it is for a restroom provider to buy and install rolls of sanitary napkins, the quicker they will become common. If they are free and common, but not fancy, then women are more likely to use them sparingly, and only for emergencies.

In one aspect, the invention features a strip having a weakened region that defines first and second segments on either side thereof. The first and second segments include corresponding first and second sanitary napkins.

Some embodiments also include a core with the strip having been wound around the core and with the strip's end having been attached to the core.

Also among the embodiments are those in which the first segment includes layers adhesively bonded to each other with the sanitary napkin disposed between them. In such embodiments, peeling apart the layers enables removal of the first sanitary napkin from the first segment.

In yet other embodiments, the first segment includes a layer and the sanitary napkin has a first face that attaches to the layer. In such embodiments, the second face, which is opposite the first, is exposed.

Among the embodiments are those in which the sanitary napkins has parallel faces separated by a layer that has an exposed side. This exposed side is an exposed edge of the layer.

Also among the embodiments are those in which the sanitary napkin has a hidden edge. In such embodiments, the sanitary napkin includes parallel faces separated by a layer. The parallel faces join each other at a margin that surrounds the layer. This prevents the layer from being exposed. As a result, the layer's edge remains hidden.

Some embodiments have a strip that has a variable width. Among these are embodiments in which notches have been formed in the strip.

In other embodiments, the strip is narrowest at the weakened region and widest within the first and second segments.

Some embodiments also include a cylinder having an annular cross section with the strip having been wound around the cylinder. Among these are embodiments in which the cylinder is made of cardboard.

In still other embodiments, the first sanitary napkin includes a liquid-absorbing layer that includes a superabsorbent polymer.

Other embodiments include those in which the first sanitary napkin is die cut.

In some embodiments, the first sanitary napkin includes an impervious layer, an adhesive layer, and an absorbent layer. In such embodiments, the impervious layer is between the adhesive layer and the absorbing layer, the strip includes a base layer that adheres to the adhesive layer, and the base layer is wider than the first sanitary napkin.

Also among the embodiments are those in which the first sanitary napkin includes a first impervious layer that is between an adhesive layer and an absorbing layer. The strip includes a base layer that adheres to the adhesive layer. The base layer is wider than the first sanitary napkin. The second impervious layer is attached to the base to form a margin around the first sanitary napkin.

Embodiments further include those in which the weakened region includes perforations through the strip and those in which, at the weakened region, a multiplicity of connecting filaments connect the first and second segments. In these latter embodiments, a sum of widths of the filaments is less than the width of the strip. Also among these embodiments are those in which a webbing connects the first and second segments to each other at the weakened region.

In some embodiments, the first segment includes thermally-bonded first and second layers with the first sanitary napkin disposed between them. In such embodiments, peeling apart the first and second layers enables removal of the first sanitary napkin from the first segment.

Embodiments further include those in which a peel-off backing matches the napkin's width. Among these are embodiments in which the first segment includes a layer and the sanitary napkin has a face that is attached to the layer such that peeling off the layer exposes the face. In such embodiments, the layer and the sanitary napkin have a common width.

Additional embodiments include those in which the first segment includes a layer having a message region on which a promotional message can be or is imprinted. The sanitary napkin has a face that is attached to the layer such that peeling off the layer exposes the face. Other features and advantages of the invention are apparent from the following description, and from the claims.

Individually die-cut sanitary napkins can be economically placed on a strip and rolled on a core if the standard backing strip that covers the adhesive is extended out to be the carrier or backing that would be perforated and then rolled on a paper tube. A cover could also be added so that each sanitary napkin is fully enclosed after it is separated by the perforation on the roll.

This represents the cleanest and best-featured solution, but also the most expensive. This version may be used in luxury facilities, which may even print their compliments on the covering layer.

What follows is a series of variations that will progressively save on cost by removing material or manufacturing complexity, along with features that seek to maximize function and cleanliness.

Individual die-cut napkins are ideally shaped and cut out of a continuous assembly. The extra material is discarded. The manufacturing process that places this individual napkin on a backing requires a well-timed step. If the sanitary napkin is destined to be rolled on a core, then it makes sense modify the design to be a continuous strip when on the core. This saves on material and process complexity.

Since a sanitary napkin is primarily rectangular in shape, the design of a free product could be compromised to actually be rectangular, with the short ends having a perforated edge that results after separation. A die-cut that creates the perforation would also punch out the corners of the rectangular shape so that it is more comfortable when in use.

In a significant process simplification, one die-cut step could create the perforation and cut out through all layers of an assembly with cover as the last step before rolling on to a core. Thus, no special timing is needed to synchronize steps of the process because up until the last die-cutting step, it is a continuous assembly.

One version would have the backing for the adhesive extend past the width of the sanitary pad assembly to be the base, then a cover could be heat sealed or adhered to the base, then the whole assembly punched to create a shape and perforation, creating a mostly sealed product.

In another version, there would be no cover, and the strip would be rolled such that the base, which would preferably be a plastic sheet, is on the outside to protect the absorbing side of the pads. This saves on material, cost, and allows more napkins to be placed on a roll.

This could be enhanced by adding strips of adhesive in the margins of the base to keep the outermost napkin on the roll, so it is removed like masking tape. In this way, there is nothing hanging down and exposed, otherwise users may be tempted to discard the first sheet if they see an exposed sanitary napkin.

There are many ways to punch out the corner of the napkin, or a cut can be made instead of punch, so there is no punch-out to be removed in the manufacturing process. Instead, the corner remains on the base layer after the sanitary napkin is removed.

In a further cost reduction, the base layer is the same width as the sanitary napkin. This saves a little on material, but more significantly, the thickness is consistent across the width, so the roll may be neater. Also, if a roll is under fifty millimeters in width, then two could fit on a standard toilet paper dispenser. As with previous variations, the base would be rolled on the outside to protect the absorbing layer and it could have optional adhesive strips on the back to prevent the outermost sanitary napkin from hanging down and becoming exposed.

The least expensive version would have no base, and the adhesive would stick to the opposite absorbing side when rolled. With proper construction, and perhaps the use of two strips instead of complete coverage, the sanitary napkin would come off the roll like masking tape without damage. With one less layer, more sanitary napkins will fit on a roll.

Because this is a free item, it may be acceptable to use super absorbing polymers or hydrogels. These can be sprayed on in a powder and can hold thirty to sixty times their volume, resulting in a feminine napkin that could be only half a millimeter thick, compared to luxury toilet paper that is three tenths of a millimeter thick. With this capacity for number of napkins per roll, the utility and economy approaches toilet paper, and it may be possible for the absorbing side to be exposed when rolled. This version would benefit from being mounted in a covered dispenser. Otherwise, the impervious side of the feminine napkin would be on the outside of the roll.

In some embodiments, the strip has a central section and margins on either side of the central section. Because of a difference in thicknesses of materials, this forms a gap on either side of the central section. The thickness of this gap depends on the thickness of the central section of the strip. Among the embodiments are those in which steps have been taken to eliminate this gap. These include embodiments in which the margins have been folded to close the gap and those in which a spacer material has been inserted into the gap.

These and other features of the invention will be apparent from the following detailed description and the accompanying figures, in which:

DETAILED DESCRIPTION

Figure 1:
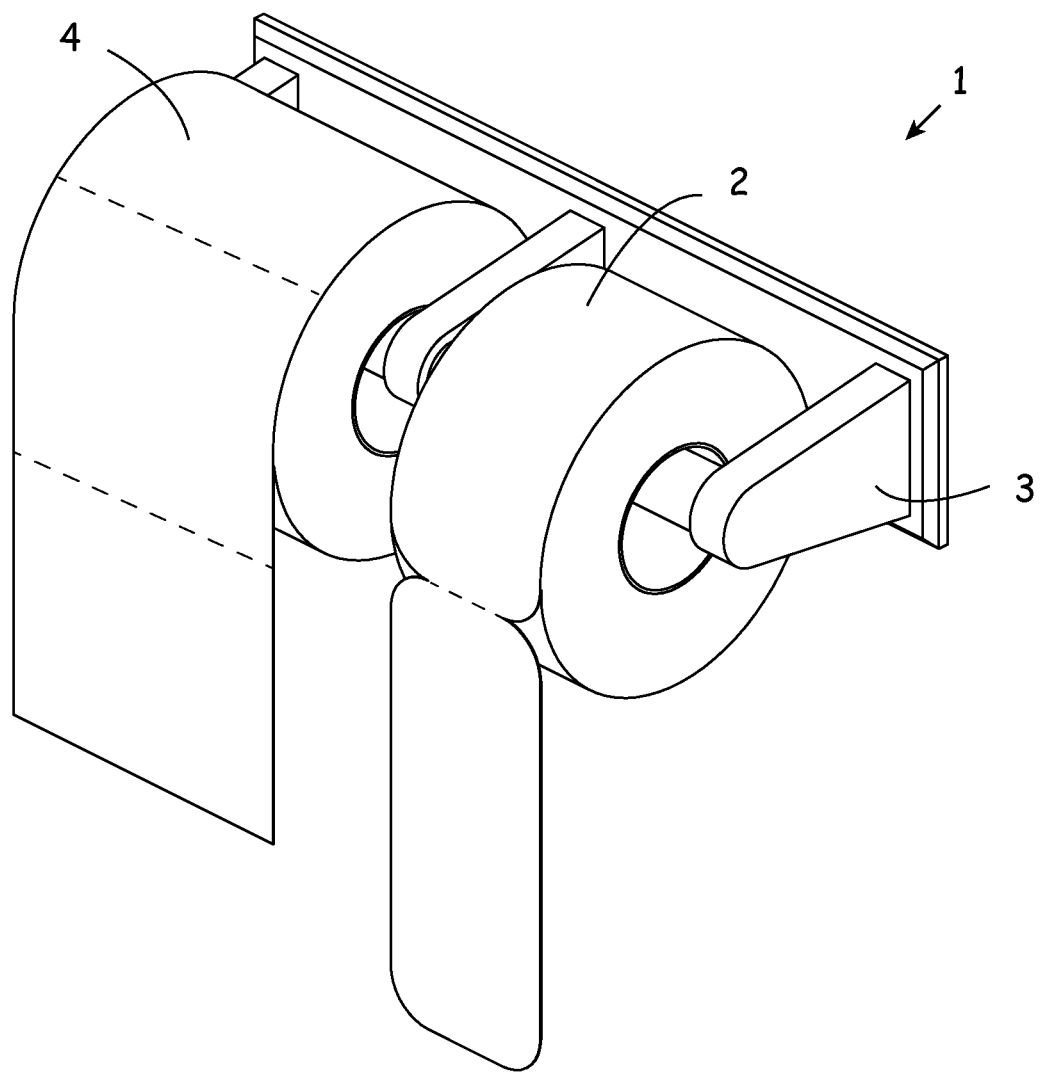
FIG. 1 is a depiction of a toilet paper dispenser holding two rolls: one of toilet paper, and one of sanitary napkins.

Referring to FIG. 1, a solution for providing sanitary napkins 10 in a public restroom with minimal investment includes a roll 2 of sanitary napkins 10 that can be mounted on a standard dispenser 3 in the same way that ordinary toilet paper rolls 4 are mounted.

Figure 2:
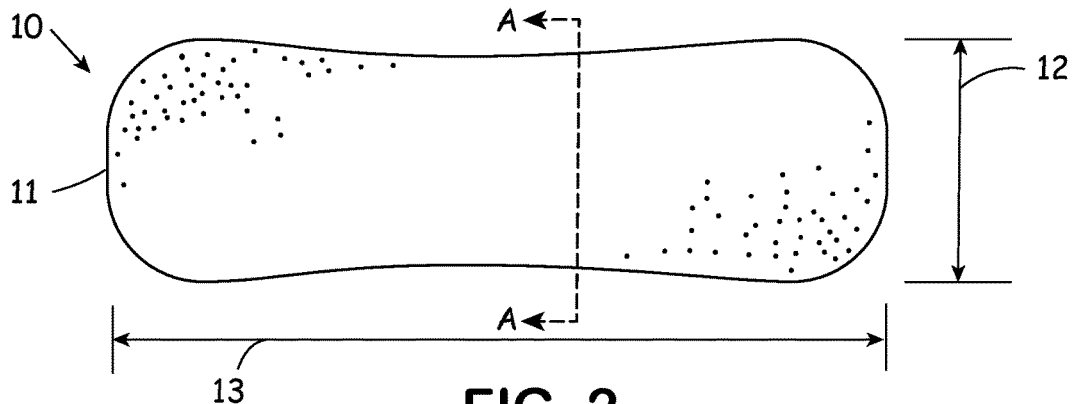
FIG. 2 is a representation of a die-cut sanitary napkin with adhesive exposed that is ready for attachment to an undergarment.

Referring to FIG. 2, a typical die-cut sanitary napkin 10 that is ready to be applied has a die-cut shape 11. The sanitary napkin 10 has a width 12 that is between thirty and sixty millimeters and a length 13 that is between one hundred forty and two hundred millimeters.

Figure 2A:
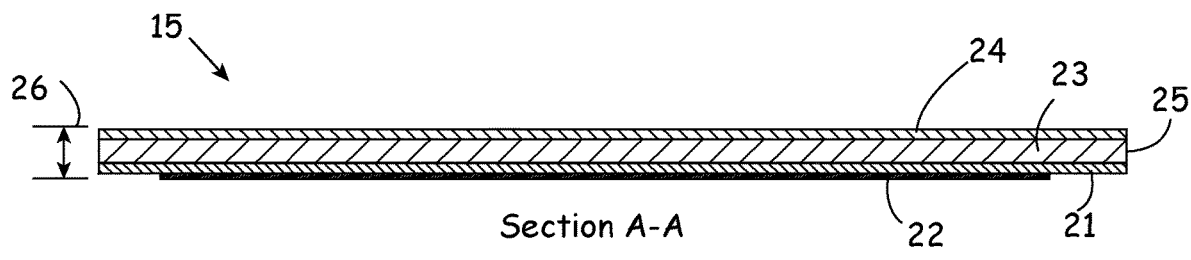
FIG. 2A is a cross section of the sanitary napkin of FIG. 2 showing the functional layers and where the edges are not sealed such that the absorbing layer is exposed at the edges. All cross-section thicknesses are scaled to be larger relative to the width for clarity of illustration.

Referring to section A-A in FIG. 2A, the layers of a typical die-cut sanitary napkin 15 include a backing layer 21 of fluid-impervious material with pressure sensitive adhesive 22 attached to one face, a layer of fluid-absorbing material 23 attached to the opposite face, and a layer of fluid-absorbent fabric 24 attached to the opposite side of the fluid-absorbing material 23. The overall thickness 26 is generally between half a millimeter and two millimeters.

In some embodiments, the edge of the sanitary napkin 10 has been die-cut. This creates an edge 25 that exposes the fluid-absorbing material 23. Embodiments include those in which the fluid-impervious material of the backing layer 21 is made of low density polyethylene film and those in which the fluid-absorbing material 23 is made of cotton or cellulose.

Figure 2B:
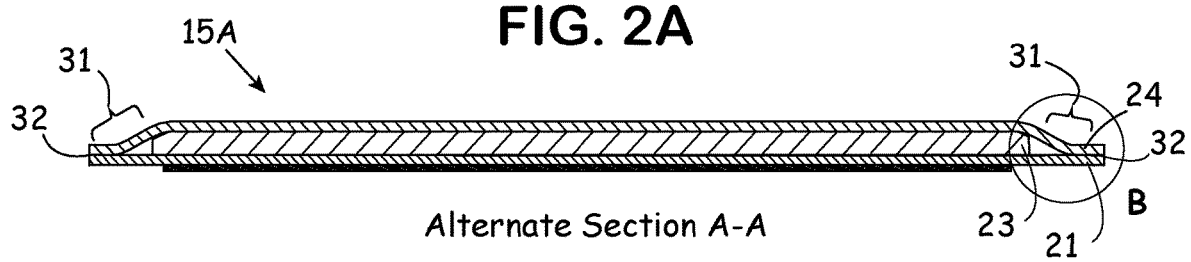
FIG. 2B is a cross section of an alternate sanitary napkin of FIG. 2A where the ends have been sealed and absorbing layer is not exposed at the edges.

Referring to alternate section A-A in FIG. 2B, the layers 15B of an improved die-cut sanitary napkin include a margin 31 in which there is no fluid-absorbing material 23. At the margin 31, the fluid absorbing fabric 24 and the backing layer 21 are bonded to form an edge 32. This edge 32 prevents fluid from spreading out to the sides and going beyond the backing layer 21. This helps avoid leakage of fluids.

Figure 2C:
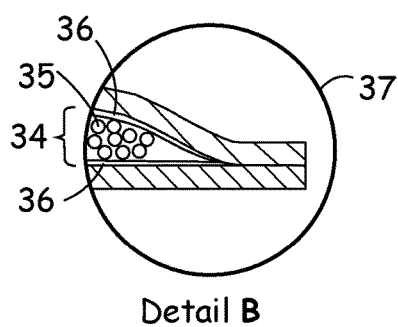
FIG. 2C is a detail of the cross-section FIG. 2B representing an absorbing layer made of up a super-absorbent polymer and other layers to contain the polymer.

Referring to Detail B of FIG. 2C, a layer 34 of fluid-absorbing material 23 is disposed between two sheets of fabric 36. In some embodiments, the fluid-absorbing material 23 comprises super-absorbing polymer 35. A super-absorbing polymer 35 can absorb three hundred times its weight and thirty to sixty times its volume of water. It can be sprayed on as a powder, sometimes called slush powder, in a continuous operation. This results in extremely thin pads that can absorb as much fluid as thicker pads that use cotton or cellulose. As a result, it becomes possible to place many more pads on a roll. This promotes cost savings.

Figure 3:
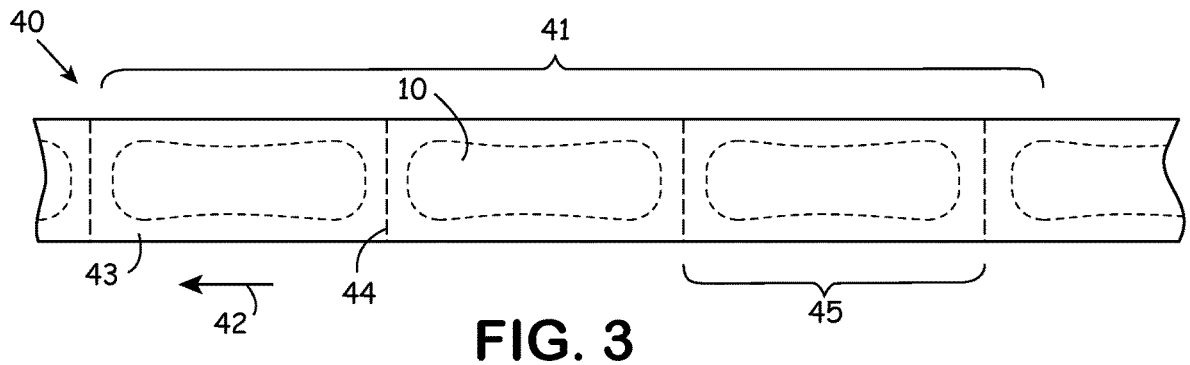
FIG. 3 is an illustration of a continuous strip of the die-cut sanitary napkins of FIG. 2 placed between two layers of material at regular intervals with a perforation between die-cut sanitary napkins along the strips.

Referring to FIG. 3, a continuous strip 40 of die-cut sanitary napkins includes a series 41 of die-cut sanitary napkins 10 placed at regular intervals along the strip's longitudinal direction 42. The napkins 10 lie between two continuous strips of material 43 with a perforation 44 through all layers of the continuous strip 40. These perforations 44 allow a segment 45 or number of segments 45 to be separated from the continuous strip 40.

Figure 3A:
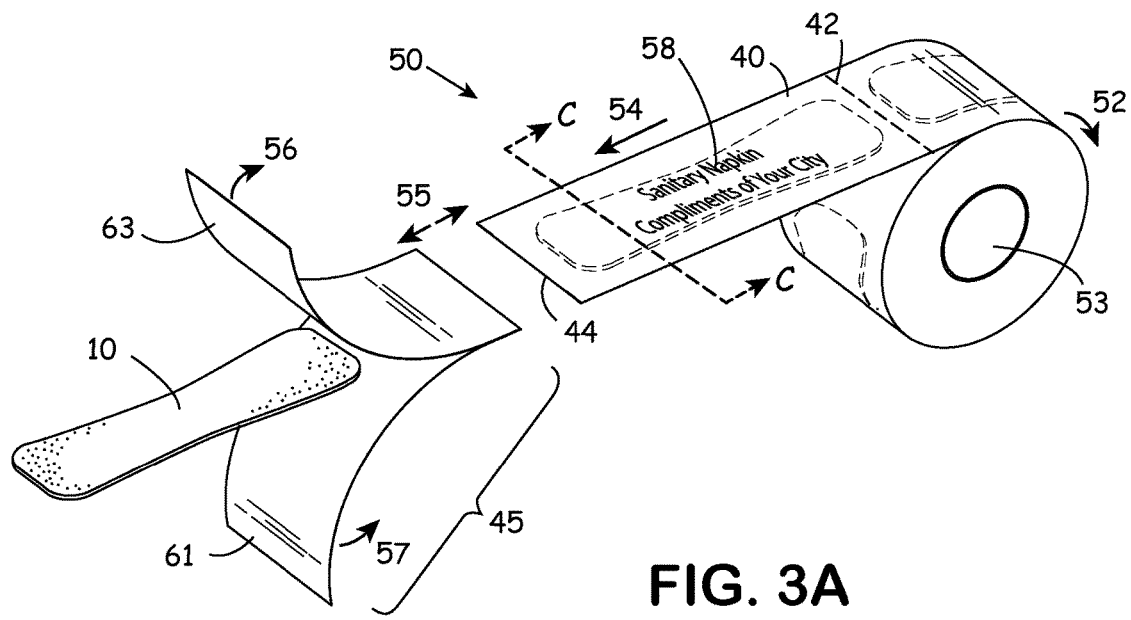
FIG. 3A is a representation of a roll of continuous strip of die-cut sanitary napkins where the continuous strip of FIG. 3 is wound on core and can be unwound by a user, with a segment of the continuous strip separated at the perforation, and the die-cut sanitary napkin therein removed from the continuous strip.

Referring to FIG. 3A, after having been fabricated, the continuous strip 40 of die-cut sanitary napkins 50 is rolled onto a core 53 to form a roll 52. Once the roll 52 is installed near a toilet, a user unrolls it, separates a segment 45 from the strip 40 at the perforations 44, removes the layers of the continuous strip 40, and exposes the die-cut sanitary pad 10 for application to an undergarment.

The core 53 is preferably a cardboard tube. In some embodiments, outer layer of material 58 forms a rolling billboard on which messages, such as advertising messages, can be printed.

Figure 3B:
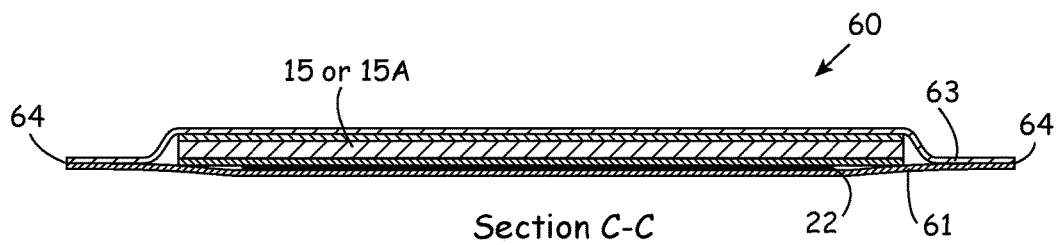
FIG. 3B is a cross section of the continuous strip of FIG. 3A showing the sanitary napkin placed between the two layers of material.

Referring to Section C-C in FIG. 3B, the layers 60 of the continuous strip 40 include a base layer 61 and a cover layer 63. The base layer 61 is a layer of fluid-impervious material, such as low density polyethylene film that is attached to the adhesive strip 22 of the die-cut sanitary napkin with layers 15, 15A. The cover layer 63 is a layer of a fluid-impervious material that has been attached to base layer 61 via adhesive, deformation, heat seal, or some other attachment method 64. The base layer 61 and the cover layer 63 cooperate to keep the sanitary napkin clean and will minimize the chance of water incursion.

Figure 4:
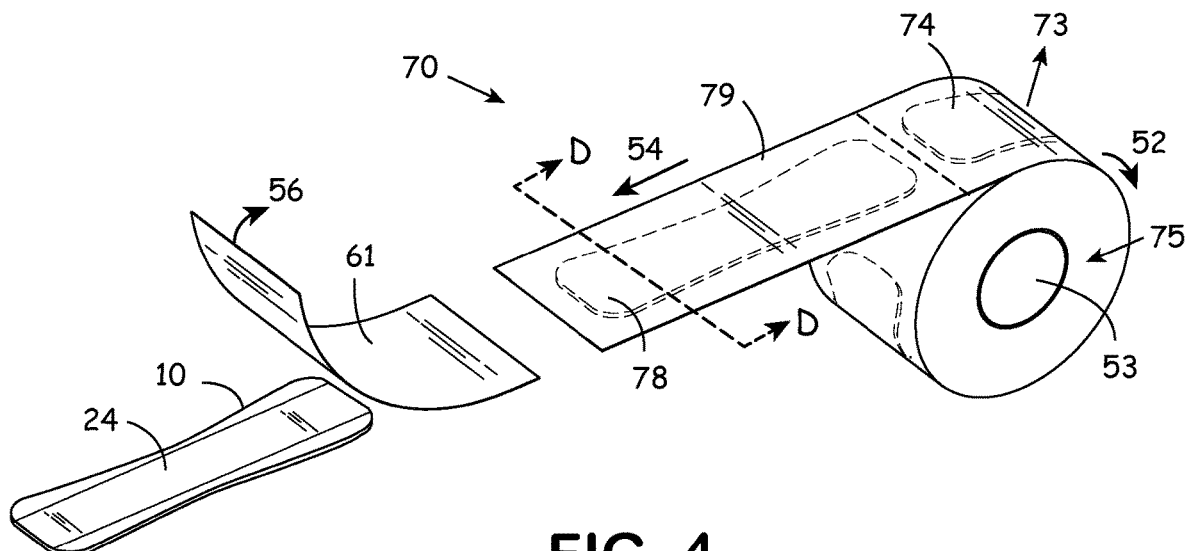
FIG. 4 is a variation of the roll of continuous strip of die-cut sanitary napkins of FIG. 3A where one layer of continuous strip has been removed, and the remaining continuous strip layer is attached on the adhesive side of the sanitary napkin, and is wound such that the continuous strip layer is distal relative to the core so that it acts to cover the sanitary napkin from exposure.

FIG. 4 shows a lower cost embodiment that requires less raw material to make. In this embodiment, the layers 70 have a continuous strip of die-cut sanitary napkins 10 with only a base layer 79 rolled 52 on to core 53. The base layer 61 faces outward 73 relative to the roll. This prevents exposure of the die-cut sanitary napkins 10 on the outside circumference of the roll 74 and thereby suppresses the risk of soiling.

Figure 4A:
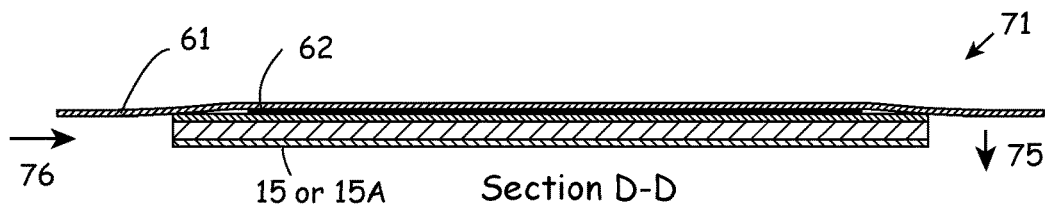
FIG. 4A is a cross section of the continuous strip of FIG. 4 showing the continuous strip orientation and attachment to the die-cut sanitary napkin.

Referring to section D-D of FIG. 4A, the layers 71 of the continuous strip 79 are oriented such that the base layer 61 is distal to the sanitary napkin with layers 15, 15A relative to core 75 before rolling 52 on to the core. A disadvantage of this embodiment arises from the edges of the sanitary napkin being exposed 76 while on the roll. As a result, a sanitary napkin on an unrolled section 78 would be exposed to soiling while the roll is idle.

Figure 4B:
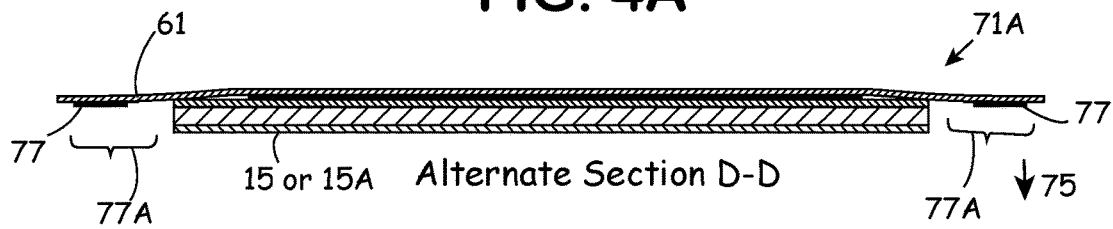
FIG. 4B is an alternate cross section of the continuous strip of FIG. 4 showing the addition of two strips of adhesive in the margin beyond the die-cut sanitary napkin that will cause continuous strip to stay attached to the roll, thereby keeping the next sanitary napkin to be removed from exposure.

Referring to alternate section D-D of FIG. 4B, the layers 71A of an improved continuous strip to a continuous strip with layers 70 will have two strips of adhesive 77 applied to the outside margins 77A of the base layer 61 on the proximal face relative to the core 75. When rolled on to a core, the base layer 61 will adhere to the layer next base layer 61 below proximal to the core. In this manner, the edges of the die-cut sanitary napkin are not exposed.

Figure 4C:
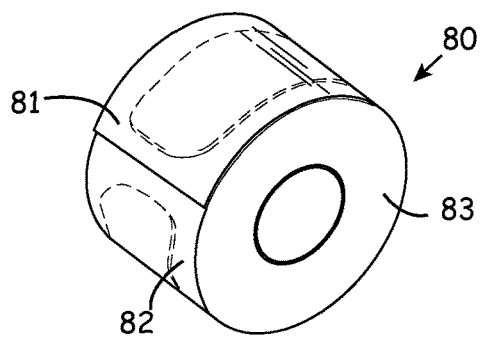
FIG. 4C is an illustration of the roll of continuous strip of die-cut sanitary napkins of FIG. 4 with alternate cross section of FIG. 4B where the continuous strip stays attached to the roll and keeps the next sanitary napkin enclosed.

Referring to FIG. 4C, an additional benefit of a roll 80 of continuous strip of die-cut sanitary napkins using a continuous strip with layers 71A is that the outermost segment 81 adheres to the outside of roll 82. As a result, the die-cut sanitary napkin in that segment does not hang down in the same way that the end of a toilet paper roll would hang down. This subtle difference helps promote the impression that the first sanitary napkin shown is as clean and as ready to use as any other sanitary napkin on the roll. As a result, the user will not feel compelled to peel off and discard a number of sanitary napkins based on a mistaken belief that those deeper in the roll are somehow more likely to be clean. This prevents waste.

Although die-cut sanitary napkins may have an ideal shape, the die-cutting process adds an extra step to the continuous assembly line. Die-cutting also produces waste.

Figure 5:
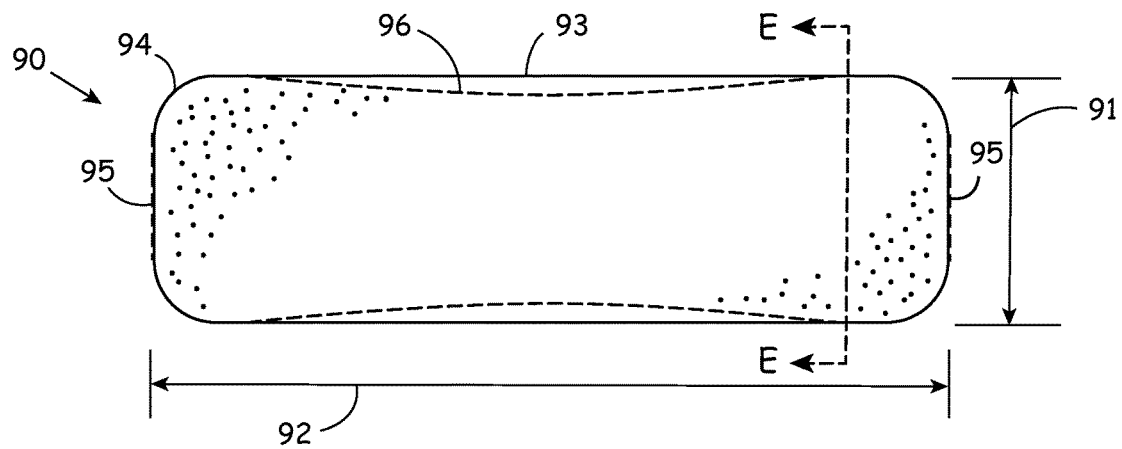
FIG. 5 is a representation of a perforated sanitary napkin created by separation from a sanitary napkin assembly that has been segmented by perforation, and that is ready for attachment to an undergarment.

Referring to FIG. 5, a cost-saving improvement to a die-cut sanitary napkin is a sanitary napkin with perforated edges 90 ready for application to an undergarment separated from a continuous strip of sanitary napkin assembly by perforation and having a rectangular shape with a width 91 between thirty and sixty millimeters and a length 92 between one hundred and forty and two hundred millimeters with a perforated edge 95 on the two shorter edges and die-cut shapes, and optionally radii 94 to remove corners that would be uncomfortable during use. The longer edge may optionally be shaped 96 by die-cutting.

Figure 5A:
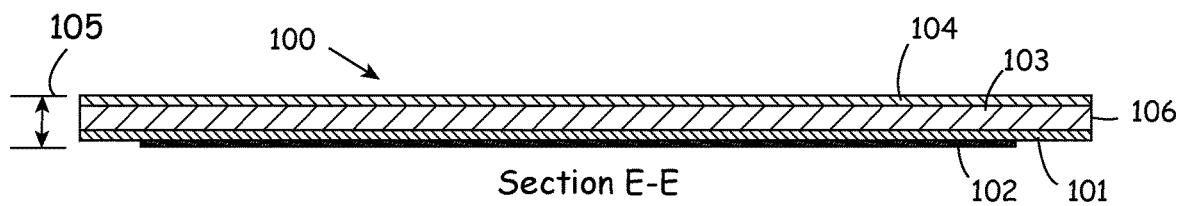
FIG. 5A is cross section of the perforated sanitary napkin of FIG. 5 showing the functional layers and where the edges are not sealed such that the absorbing layer is exposed at the edges.

Referring to Section E-E in FIG. 5A, the layers of a continuous strip of sanitary napkin assembly 100 include a backing layer 101 of fluid-impervious material with pressure sensitive adhesive 102 attached to one face, and fluid-absorbing material 103 attached to the opposite face, and absorbent fabric 104 attached to the opposite side of the fluid-absorbing material 103. The overall thickness 105 is generally thin, between half a millimeter and two millimeters, because the sanitary napkin is intended for comfort and to absorb surprise leaks. It is not intended for large menstrual fluid flow. The edge of the sanitary napkin can be die-cut, exposing 106 the fluid-absorbing material.

Figure 5B:
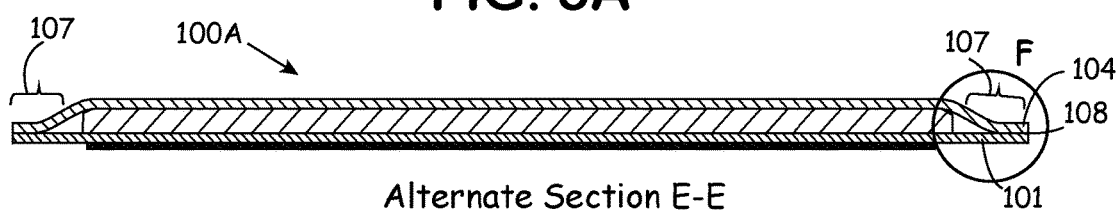
FIG. 5B is cross section of an alternate perforated sanitary napkin of FIG. 5A where the ends have been sealed and absorbing layer is not exposed at the edges.

Referring to Alternate Section E-E in FIG. 5B, the layers of an improved continuous strip of sanitary napkin assembly 100A, but with added manufacturing cost, will have a margin 107 in which there is no fluid-absorbing material 103 where fluid absorbing fabric 104 and backing layer 101 are bonded together 108 such that fluid is prevented from spreading out to the sides and going beyond the backing layer 101, and causing leakage of fluids.

Figure 5C:
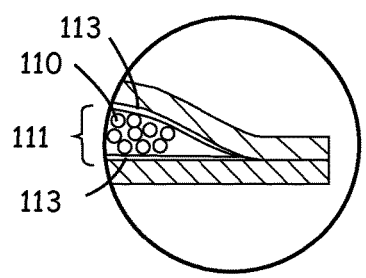
FIG. 5C is a detail of the cross-section FIG. 5B representing an absorbing layer made of up a super-absorbent polymer and other layers to contain the polymer.

Referring to Detail F of FIG. 5C the fluid-absorbing material 103 can be super absorbing polymer 110 layered 111 between sheets of fabric 113. SAP can absorb 300 times its weight, or 30-60 times its volume of water. It can be sprayed on as a powder, sometimes called slush powder, in a continuous operation, resulting extremely thin pads that can absorb as much fluid as thicker pads that use cotton or cellulose. This allows many more pads to be put on a roll with significant cost savings.

Figure 6:
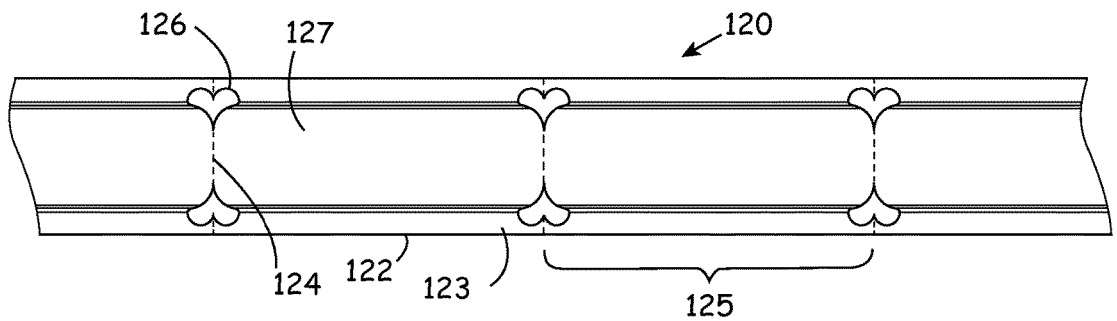
FIG. 6 is an illustration of a continuous strip of the sanitary napkin assembly of FIG. 5 that has been covered by two layers of material and then perforated and stamped at regular intervals to create segments.

Referring to FIG. 6, a segmented continuous strip of sanitary napkin assembly with cover 120 includes a continuous sanitary napkin assembly 127 placed between two continuous strips of material 122 forming a continuous strip of sanitary napkin assembly with cover that is perforated through the entire assembly 124 at regular intervals, thus forming segments 125 and die-cut 126 at the perforation location through the entire assembly to form a comfortable corner on resulting sanitary napkin with perforated edges within each segment.

Figure 6A:
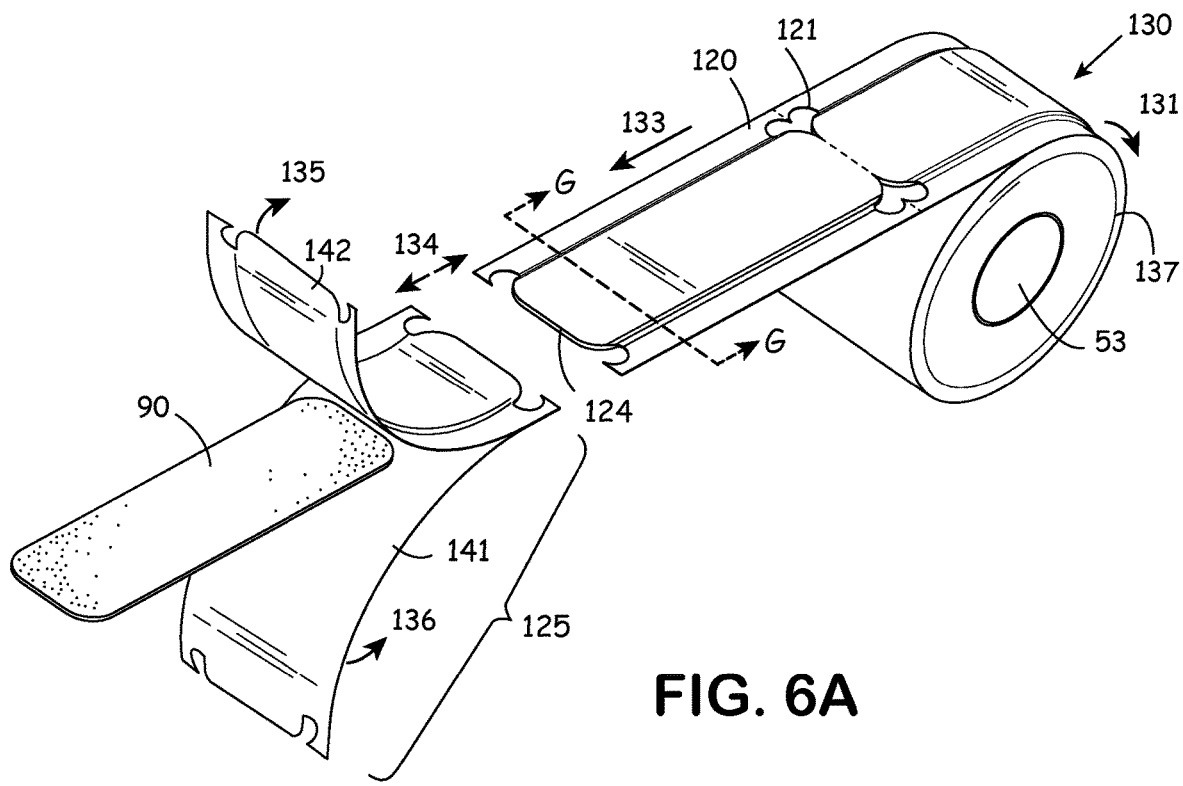
FIG. 6A is a representation of a roll of a segmented continuous strip of sanitary napkin assembly where the continuous strip of FIG. 6 is wound on core and can be unwound by a user, with a segment of the continuous strip separated at the perforation, and the perforated sanitary napkin therein removed from the covering layers.

Referring to FIG. 6A, a roll of segmented continuous strip of sanitary napkin assembly with cover 130 includes a continuous strip 120 being rolled 131 on to a core 53 after fabrication, and during use may be unrolled 133 to allow separation 134 of a segment 125 from the continuous strip 120 at the perforation 124, and then the layers of cover of continuous strip can be removed 135, 136 to expose sanitary napkin with perforated edges 90 for application to an undergarment. The core 53 is preferably a cardboard tube.

Figure 6B:
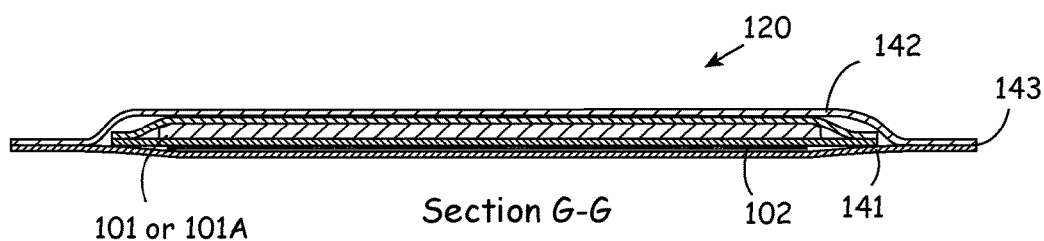
FIG. 6B is a cross section of the continuous strip of FIG. 6A showing the sanitary napkin assembly placed between the two layers of material.

Referring to Section G-G in FIG. 6B, the layers of continuous strip 120 include a base layer 141 that is attached to adhesive 102 of the sanitary napkin material with layers 100 or 100A and a cover layer 142 of fluid-impervious material that is attached to base layer 141 via adhesive, deformation, or heat seal 143. These two layers will keep the sanitary napkin dry and clean. The fluid-impervious material can be low density polyethylene film.

Figure 7:
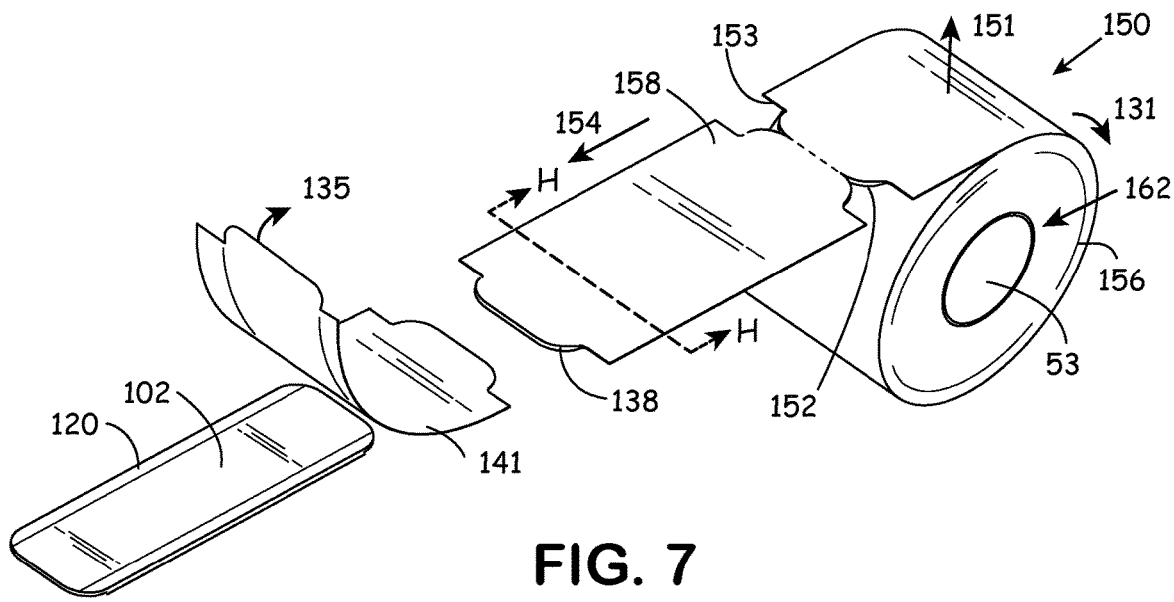
FIG. 7 is a variation of the roll of segmented continuous strip of sanitary napkin assembly of FIG. 6A where one covering layer has been removed, and the remaining layer is attached on the adhesive side of the continuous strip of sanitary napkin, and is wound such that the covering layer is distal relative to the core so that it acts to protect the sanitary napkin assembly from exposure.

Referring to FIG. 7, a cost reduced and less wasteful version 150 of a roll of segmented continuous strip of sanitary napkin assembly with cover 130 will use a segmented continuous strip of sanitary napkin assembly with cover with base layer only 158 that has only one base layer 141 and rolled 131 on to core 53 such that the base layer 141 is facing outward 151 relative to the roll. In this manner, the sanitary napkins on the outside circumference of the roll 152 will not be exposed to soiling. The die-cut shape 153 shown is an alternate shape for achieving a rounded corner on the perforated sanitary napkin.

Figure 7A:
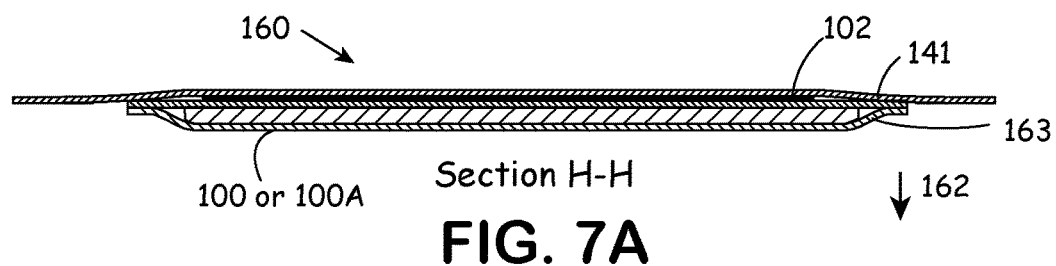
FIG. 7A is a cross section of the continuous strip of FIG. 7 showing the covering layer orientation and attachment to the sanitary napkin assembly.

Referring to Section H-H of FIG. 7A, the layers 160 of the continuous strip 158 are oriented such that the base layer 141 is distal relative to the core 162 to the sanitary napkin with layers 100 or 100A before rolling on to the core. Unfortunately, the edges of the sanitary napkin are exposed 163 while on the roll, and a sanitary napkin on an unrolled section 138 will be exposed to soiling while the roll is idle.

Figure 7B:
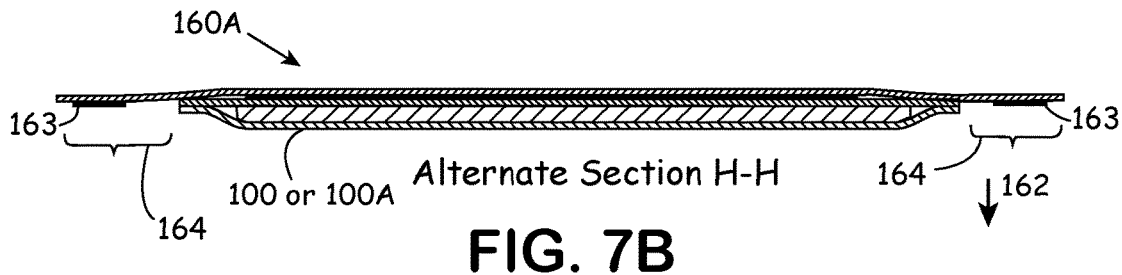
FIG. 7B is an alternate cross section of the continuous strip of FIG. 7 showing the addition of two strips of adhesive in the margin beyond the sanitary napkin assembly that will cause the covering layer to stay attached to the roll, thereby the outermost sanitary napkin segment from exposure.

Referring to Alternate Section H-H of FIG. 7B, the layers 160A of an improved continuous strip to a continuous strip with layers 160 will have two strips of adhesive 163 applied to the outside margins 164 of the base layer 141. When rolled on to a core, the base layer 141 will adhere to the layer next base proximal layer relative to the core 162. In this manner, the edges of the sanitary napkin are not exposed.

Figure 7C:
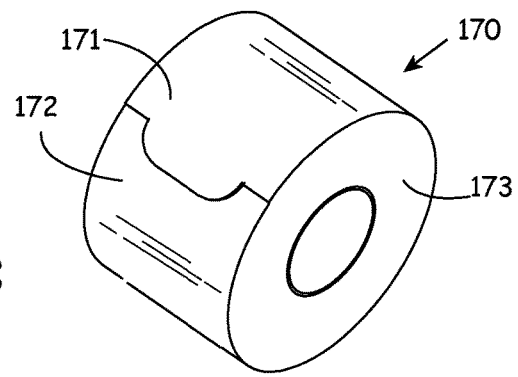
FIG. 7C is an illustration of the roll of segmented continuous strip of perforated sanitary napkin assembly of FIG. 7 with alternate cross section of FIG. 7B where the continuous strip stays attached to the roll and keeps the next sanitary napkin enclosed.

Referring to FIG. 7C, an additional benefit of a roll 170 of segmented continuous strip of sanitary napkin assembly with cover having layers 160A will be that the outermost segment 171 will adhere to the roll 172 such that the perforated sanitary napkin in that segment does not hang down and become exposed. This encourages users that the first sanitary napkin to be presented will be clean before use, and they will not feel the need to peel off a number of sanitary napkins to find one that is deeper in the roll and more likely to be clean, which would be wasteful.

Figure 8:
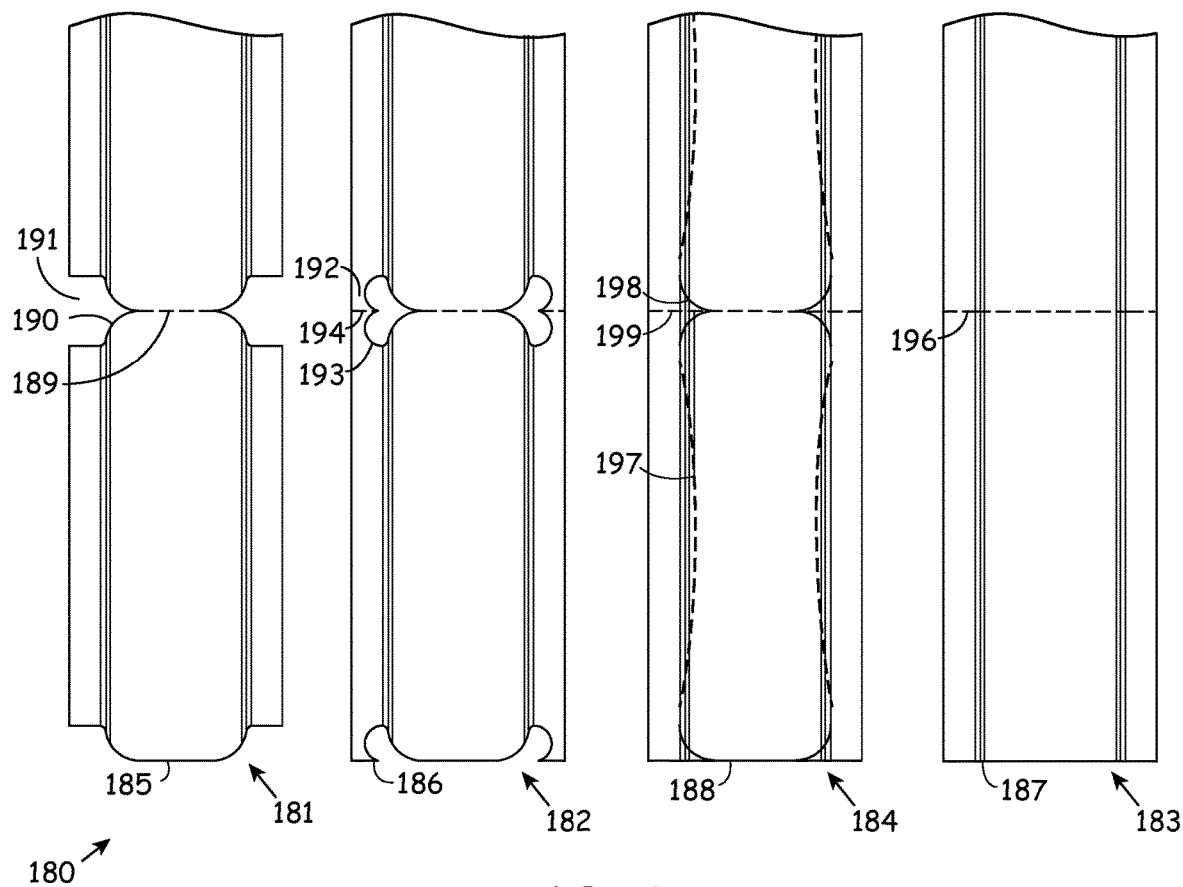
FIG. 8 is an illustration of four die-cutting designs that will perforate between and cut the corners of each sanitary napkin assembly at the same time, shown in order of diminishing material removal.

Referring to FIG. 8, a number of perforations 180 are possible for segmenting the continuous strip 120 or 158 (FIGS. 6 and 7). A large material removal method 181 will have a die-cut perforation 189 through all layers in the central area, and on the margins, a curved shape 190 will cut off the corner of the sanitary napkin, while also removing the remaining material 191 between the curved shape and the outer margin. This results in a fairly neat leading edge 185. However, the side wall on the resulting roll will have a jagged uneven side edge 156 (FIG. 7) that could become frayed. A smooth continuous edge method 182 can be achieved with less material being removed with a closed die-cut pattern 193 resulting in material at the margins 192 that will be perforated 194. This adds strength and provides a smooth continuous edge on the side of the roll 137 (FIG. 6A). However, unsupported, and delicate material is left on the leading edge 186. A segmenting method with no material removal 184 is achieved by making a curved cut across the corner of the sanitary napkin 198 with a perforation across the entire width 199. Because the die-cut shape does not form a loop, there is no material removal. There is also a resulting straight continuous leading edge 188. This method is desirable in a manufacturing setting because die-cut material will not have to be removed from the process and disposed. A variation 183 of method 184 will have a perforation only, resulting in a plain rectangular sanitary napkin with no radius at the corner 186.

Figure 8A:
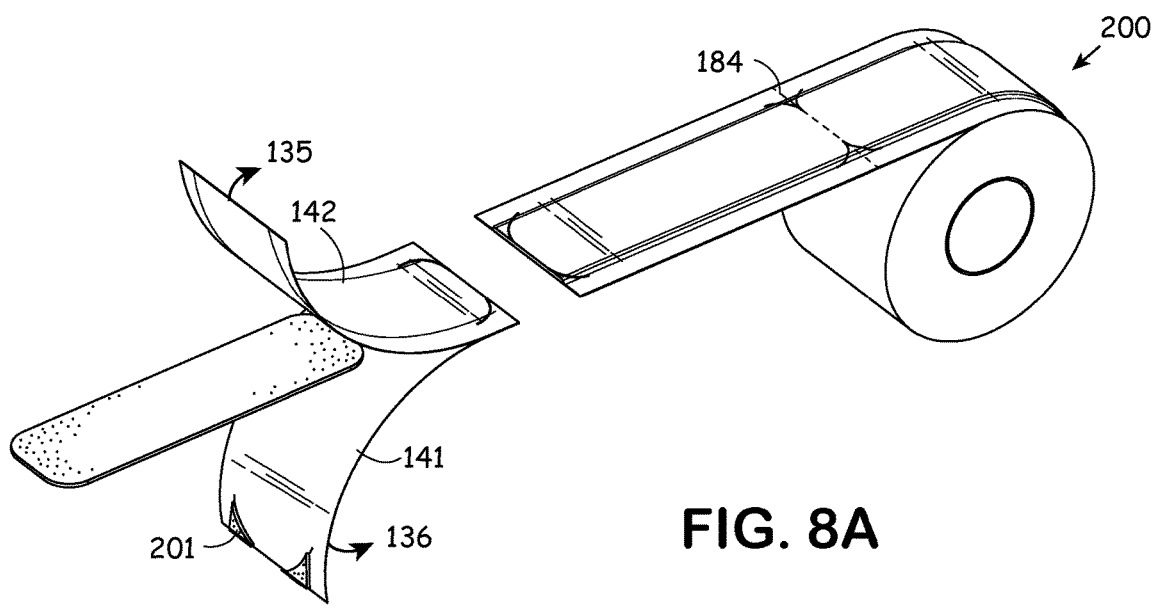
FIG. 8A is a representation of a roll of a segmented continuous strip of sanitary napkins using a method of perforation and cutting of sanitary napkin corners where no material has been removed, with a segment of the continuous strip separated at the perforation, and the perforated sanitary napkin therein removed from the covering layers, showing the die-cut corners remaining on a covering layer.

Referring to FIG. 8A, a version 200 of the rolls 130 or 150 that uses perforation method 184 would have the cut sanitary pad material corner 201 remaining on base layer 141 after it has been peeled away 136.

Figure 9:
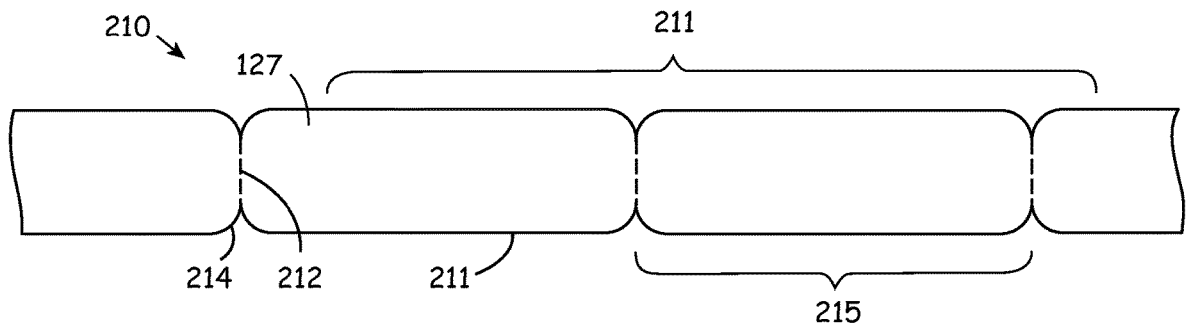
FIG. 9 is an illustration of a continuous strip of the sanitary napkin assembly of FIG. 5 with a backing layer applied to the adhesive side that has been perforated and stamped at regular intervals to create segments.

Referring to FIG. 9, a further cost reduced version of a segmented continuous strip of sanitary napkin assembly with cover 120 is a segmented continuous strip of sanitary napkin assembly with base layer 210 consisting of a continuous sanitary napkin assembly 127 with a base layer that is the same width of the sanitary napkin assembly 211 attached on the adhesive side forming a continuous strip of sanitary napkin assembly with a base layer that is perforated through the entire assembly 212 at regular intervals, thus forming segments 215, and die-cut 214 at the perforation location through the entire assembly to form a comfortable corner on the resulting sanitary napkin with perforated edges within each segment. The narrower base layer uses less material, and because it is the same width as the sanitary napkin assembly, there is no change in thickness across the width, resulting in a neater roll.

Figure 9A:
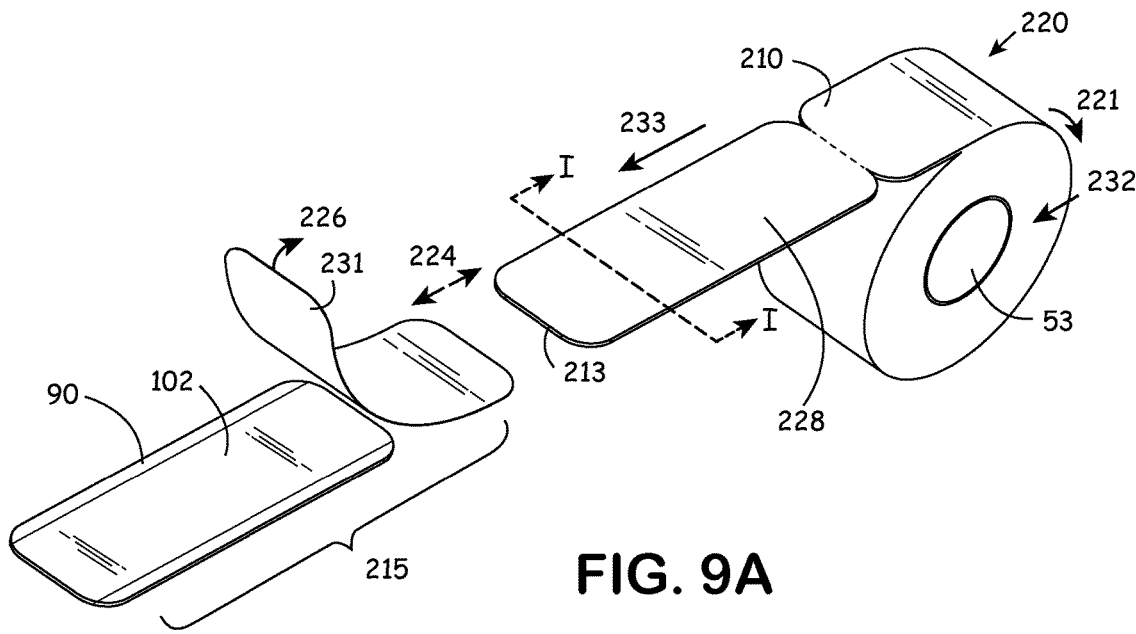
FIG. 9A is a representation of a roll of the segmented continuous strip of sanitary napkin assembly where the continuous strip of FIG. 9 is wound on core and can be unwound by a user, with a segment of the continuous strip separated at the perforation, and the perforated sanitary napkin therein removed from the backing layer.

Referring to FIG. 9A, a roll of segmented continuous strip of sanitary napkin assembly with base layer 220 includes a continuous strip 210 being rolled 221 on to a core 53 after fabrication, and during use may be unrolled 233 to allow separation 224 of a segment 215 from the continuous strip 210 at the perforation 213, and then the base layer of the continuous strip can be removed 226 to expose the sanitary napkin with perforated edges 90 for application to an undergarment. The core 53 is preferably a cardboard tube.

Figure 9B:
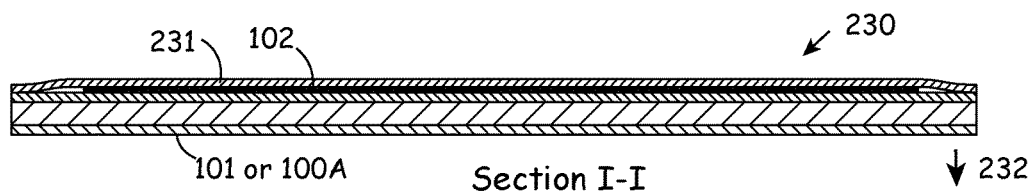
FIG. 9B is a cross section of the segmented strip of sanitary napkin assembly of FIG. 9A showing the adhesive and backing layer oriented distal relative to the core.

Referring to Section I-I of FIG. 9B, the layers 230 of continuous strip 210 are oriented such that the base layer 231 is distal 232 to the sanitary napkin assembly with layers 100 or 100A relative to the core 232 before rolling on to the core. This keeps the sanitary napkins protected. Unfortunately, a sanitary napkin on an unrolled section 228 will be exposed to soiling while the roll is idle.

Figure 9C:
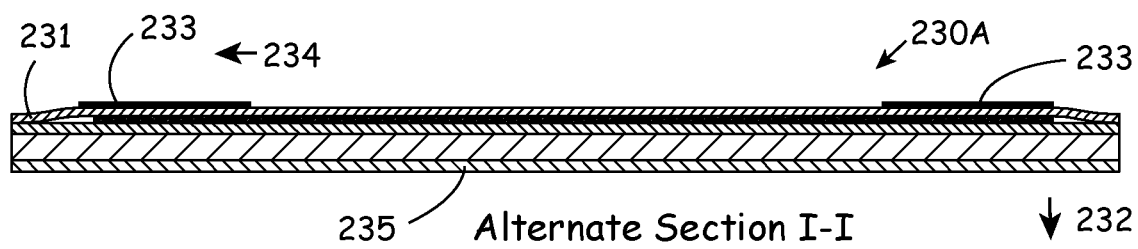
FIG. 9C is an alternate cross section of the segment strip of FIG. 9A showing the adhesive and backing layer oriented distal relative to the core, and an additional two strips of adhesive on the distal side of the backing layer.

Referring to Alternate Section I-I of FIG. 9C, an improved continuous strip with layers 230A to continuous strip with layers 230 will have two strips of adhesive 233 applied to the outside margins 234 of the base layer 231 and on the opposite side of the sanitary napkin. When rolled on to a core, the base layer 231 will adhere to sanitary napkin on the layer distal relative to the core 232, thus keeping it from separating on the roll. The adhesive is placed on the outside margin so that while on a roll, no adhesive touches the central portion 235 of an adjacent sanitary napkin that is more likely to come in contact with sensitive body tissues.

Figure 9D:
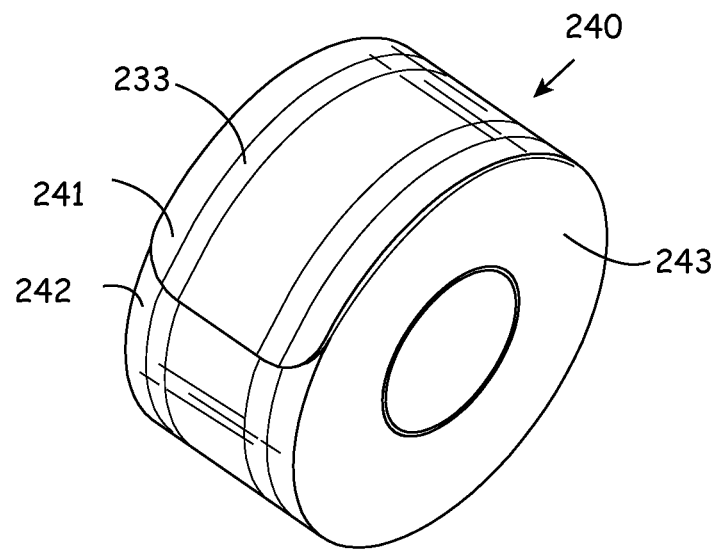
FIG. 9D is an illustration of the roll of a segmented continuous strip of perforated sanitary napkin assembly of FIG. 9 with alternate cross section of FIG. 7B where the continuous strip stays attached to the roll and keeps the next sanitary napkin enclosed.

Referring to FIG. 9D, an advantage to version 240 of a roll 220 of segmented continuous strip of sanitary napkin assembly with base having layers 230A will be that the outermost segment 241 will adhere to the roll 242 such that the perforated sanitary napkin in that segment does not hang down and become exposed. This encourages users that the first sanitary napkin to be presented will be clean before use. However, this has the disadvantage that the adhesive 233 is exposed and can gather dirt, so this version would benefit from being used in an enclosed dispenser.

Figure 10:
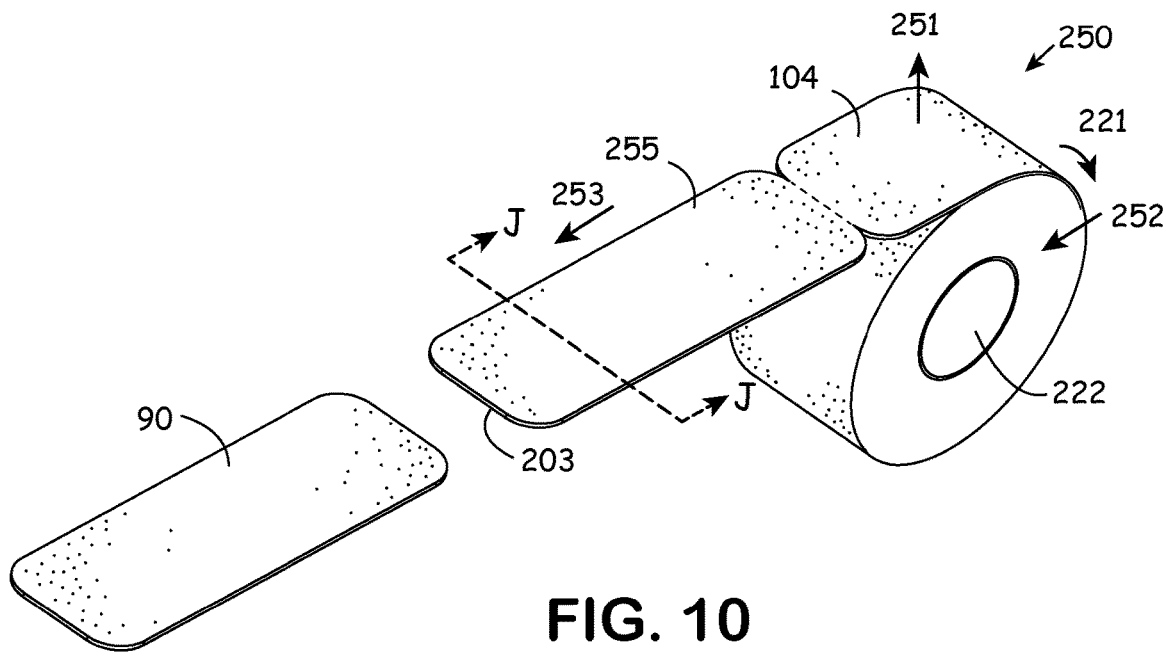
FIG. 10 is a variation of the roll of segmented continuous strip of sanitary napkin assembly shown in FIG. 9A in which there is no backing layer so that the adhesive sticks to the adjacent absorbent layers on the roll and where the absorbing layer is exposed to the outside.

Referring to FIG. 10, the least costly version 250 of a roll of segmented continuous strip of sanitary napkin assembly is a version of roll 220 without the base layer. The segmented continuous strip of sanitary napkin assembly 255 is rolled 221 on to core 53 such that the absorbing layer 104 is facing outward 251 relative to the roll. The adhesive is not exposed to the outside and therefore does not attract dirt. The strips are pulled off 253 like a roll of tape and separated so as to be made ready for application to an undergarment. Since the outermost sanitary napkins are exposed, this version is preferably used with an enclosed dispenser.

Figure 10A:
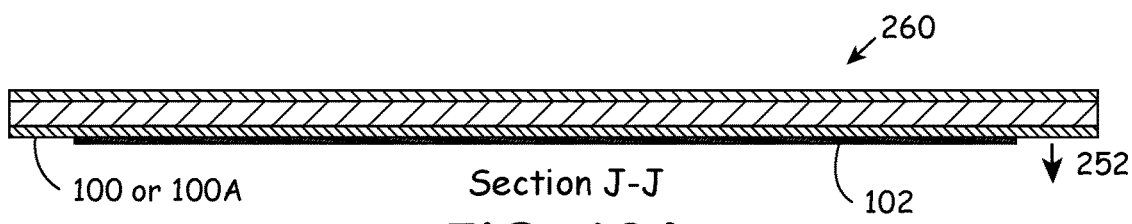
FIG. 10A is a cross section of the continuous strip of FIG. 10, showing orientation of the strip relative to the core.

Referring to Section J-J of FIG. 10A, the orientation 260 of a segmented continuous strip 255 with layers 100 or 100A is such that the adhesive layer 102 is proximal relative to the core 252.

Figure 10B:
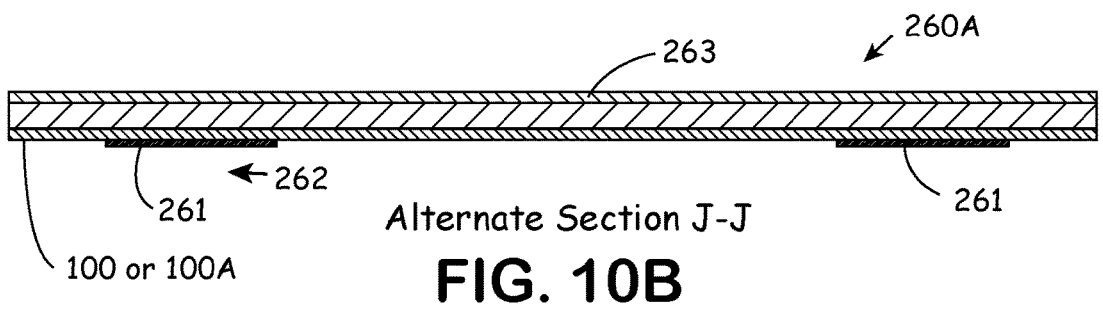
FIG. 10B is a variation of the cross section of FIG. 10A where the adhesive is in two strips so that no adhesive touches the central part of adjacent absorbing layers on the roll where contact is more likely on the more sensitive parts of the body.

Referring to Alternate Section J-J of FIG. 10B, the layers 260A of an improved continuous strip 255 with layers 260 is the removal of adhesive in the central part of the width, and applying two strips of adhesive 261 on the outside margins 262 so that when on a roll, no adhesive touches the central portion of an adjoining sanitary napkin 263 which is more likely to come in contact with sensitive body tissues.

Figure 10C:
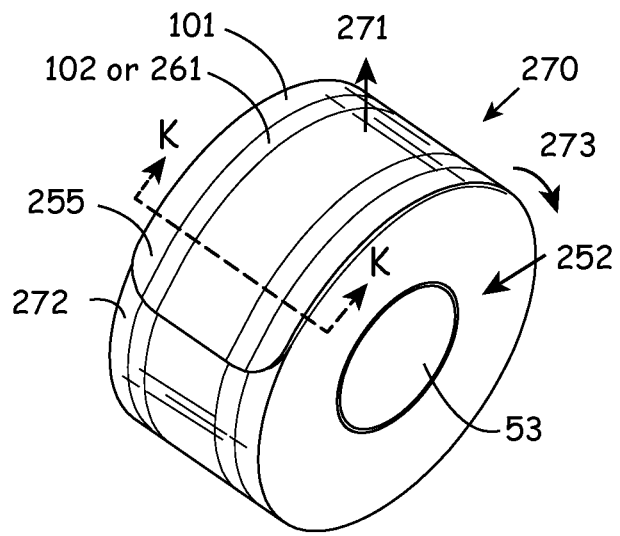
FIG. 10C is a variation of the roll of continuous strip of sanitary napkins of FIG. 10 where the adhesive layer is exposed to the outside.

Referring to FIG. 10C, an alternative roll with equivalent cost 270 to roll 250 is one where the segmented continuous strip of sanitary napkin assembly 255 is wound on the roll such that the impervious layer 101 is oriented to the outside 271 of the roll. The adhesive 102 or 261 keeps the outermost segment attached to the roll 272, so the user may perceive this version as more sanitary, even though adhesive is exposed. If the adhesive is mild enough, it may not attract much dirt, so this may be the preferred version. However, it would benefit from being used in an enclosed dispenser.

Figure 10D:
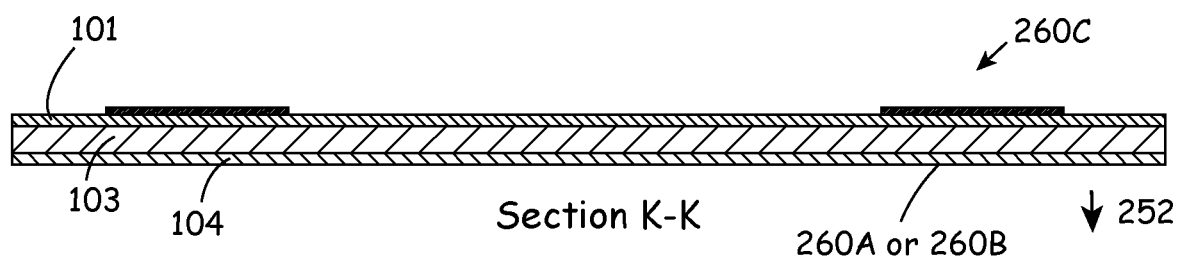
FIG. 10D is a cross section of FIG. 10C showing the orientation of the continuous strip relative to the core.

Referring to Section K-K of FIG. 10D, the orientation 260C of continuous strip 255 with layers 260A or 260B is such that the impervious layer 101 is distal relative to the core 252. In this manner, the absorbent layers 103 and 104 are covered by the impervious layer 101 while on the roll.

Figure 11A:
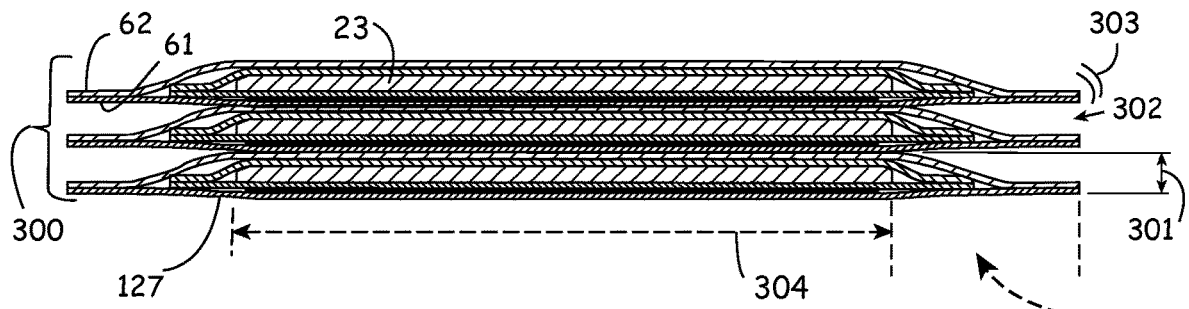
FIG. 11A is stack of the cross sections of FIG. 6B that would result after having been rolled on a core showing how the outside margins of material are unsupported by adjacent layers because they are thinner than the main section of the continuous strip of sanitary napkins.

Referring to FIG. 11A, the resulting stack 300 after a continuous strip of sanitary napkin assembly 127 has been wrapped around a roll will be much thicker at the main section 304 than it would be at the outside margin 305. This thickness 301 arises because impervious layers that extend to the margins are typically substantially thinner than central absorbing or fabric layers. In typical embodiments, the latter have a thickness of between 0.4 and 0.6 millimeters whereas the former have a thickness of only about 0.02 millimeters to 0.04 millimeters.

The resulting gaps 302 between layers in the stack will allow material to be deformed and folded over 303. This could result in an unsightly roll. The resulting gaps 302 could also trap dirt. Additionally, there is the potential of the gaps 302 becoming caught on external features while unrolling.

Figure 11B:
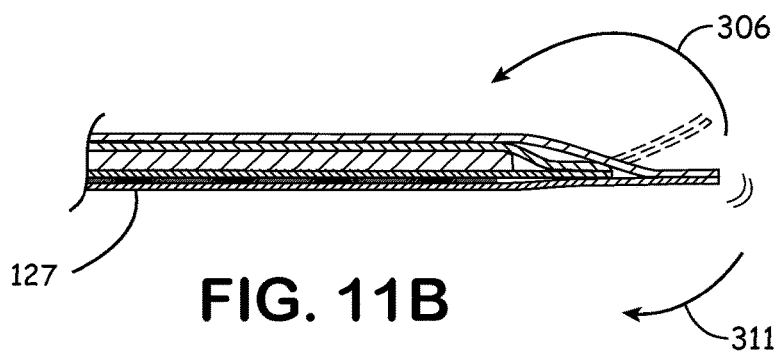
FIG. 11B is a view of one margin of one cross section in FIG. 11A showing a mechanical fold of the outside margin of thinner materials.
Figure 11C:
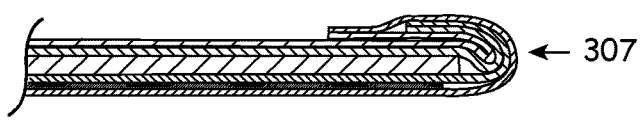
FIG. 11C is an after view of the mechanical fold of FIG. 11B showing a folded edge that is substantially equal to the thickness of the main portion of continuous strip of sanitary napkins.

Referring to FIG. 11B and FIG. 11C, a solution for this problem is to fold the thin margin material, either with an upward fold 306 or a downward fold 311. In either case, this results in an outward facing edge 307, best seen in FIG. 11C, that is substantially the same thickness as the main section 304.

Figure 11D:
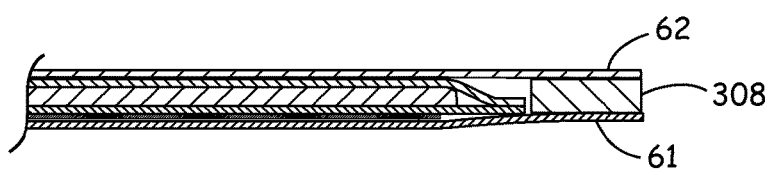
FIG. 11D is an alternate solution for supporting the outside thin material of FIG. 11A by a spacer strip that would increase the thickness of the outside margin to be equivalent to that of the main portion.

Another solution to the problem of the gap 302 is that shown in FIG. 11D. In this case, a strip of spacer material 308 has been bound between the base layer 61 and cover layer 62.

Figure 11E:
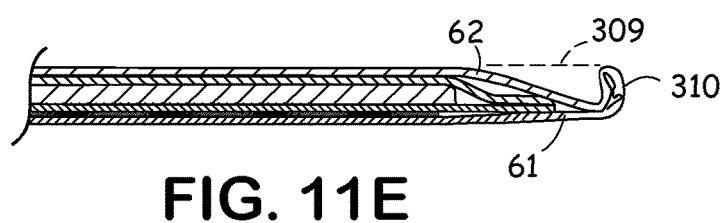
FIG. 11E is an alternate solution for supporting the outside thin material of FIG. 11A by rolling, bundling, deforming, or melting to obtain a thickness that is equivalent to that of the main portion.

Yet another solution, which is shown in FIG. 11E, is to deform, or roll, or heat the base layer 61 and the cover layer 62 such that the resulting geometry 310 is substantially the same thickness 309 as the main section.

Figure 12A:
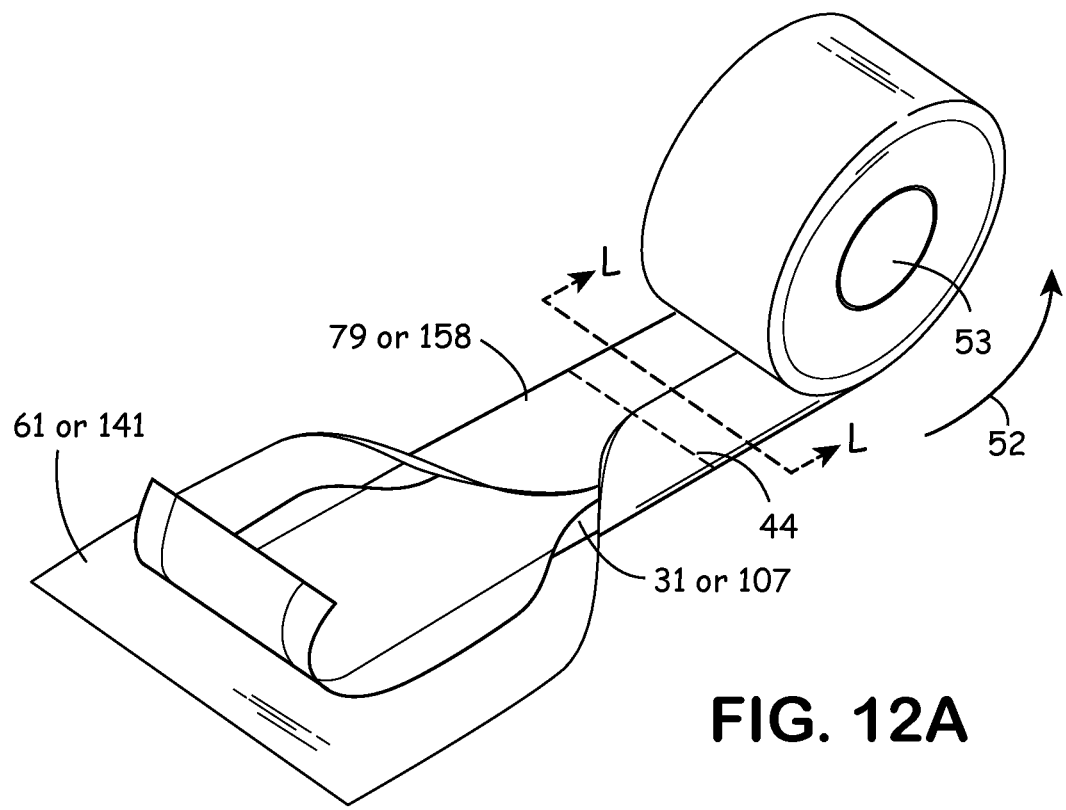
FIG. 12A shows a way to avoid having unsupported material on the outside margins by having a single external base layer be folded over and preferably overlapped on the opposite side before the continuous strip of sanitary napkins is rolled on to a core.
Figure 12B:
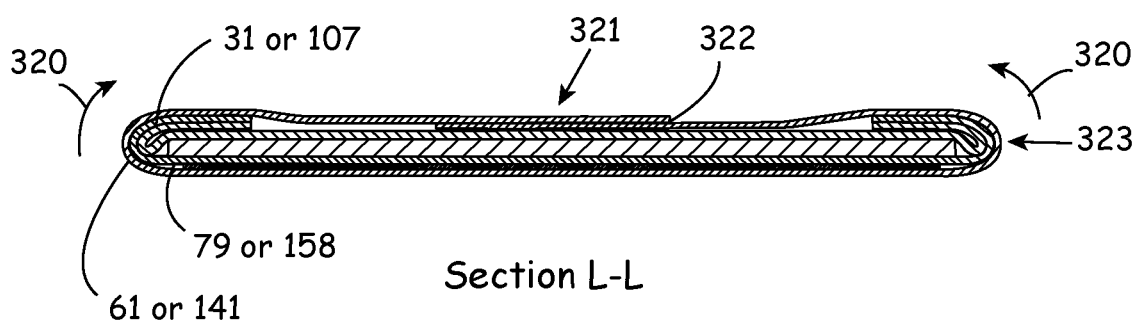
FIG. 12B is a cross section of the continuous strip of FIG. 12A showing the outer single layer having been folded over to enclose the continuous strip of sanitary napkin and also showing how the outside margin of the sanitary napkin within can also be folded over.

Referring to FIG. 12A and Section L-L of FIG. 12B, the base layer 61 of a continuous strip of die-cut sanitary napkins with only a base layer 79 or base layer 141 of a segmented continuous strip of sanitary napkin assembly with cover and base layer only 158 can be made wide enough so that it can be folded over 320 the opposite side and optionally overlapped with itself. The resulting assembly can be perforated through 44 before being rolled 52 on to a core 53.

Because margins 31, 107 of sanitary napkins are relatively thin, they too can be folded. This results in a neat outside edge 323 that presents a barrier for water ingress over a mechanical deformation between two sheets. A mechanical deformation will hold two sheets together but will not prevent water ingress.

The tension in the roll should be adequate for keeping folds 320 in place. However, in some embodiments, adhesive 322 binds the overlapping layers 321.

The details of an economical manufacturing method of these rolls such as materials, bonding, adhesives, methods for attachment to a roll, perforating, and die-cutting have been left out for clarity, and it is assumed that those skilled in the art of continuous fabric or paper manufacturing should be able to produce the rolls described.

It is to be understood that the foregoing description is intended to illustrate and not to limit the scope of the invention, which is defined by the scope of the appended claims. Other embodiments are within the scope of the following claims.

What is claimed is:

1. A manufacture comprising a core and a strip having a weakened region that defines first and second segments on either side thereof,
    said strip extending along a longitudinal direction,
    wherein said first segment comprises a first sanitary napkin and said second segment comprises a second sanitary napkin, both of which comprise absorbent layers that lie entirely flat on their respective segments, said absorbent layers being unfolded,
    wherein each of said sanitary napkins further comprises an impervious layer and an adhesive layer,
    wherein said impervious layer is between said adhesive layer and said absorbing layer,
    wherein said strip comprises a base layer that adheres to said sanitary napkin,
    wherein said base layer is wider than said sanitary napkin along a direction transverse to said longitudinal direction,
    wherein said strip is wound around said core, and
    wherein an end of said strip is attached to said core.

2. The manufacture of claim 1, wherein said first segment comprises first and second layers, wherein said first sanitary napkin is disposed between said first and second layers, wherein said first and second layers are adhesively bonded to each other, and wherein peeling apart said first and second layers enables removal of said first sanitary napkin from said first segment.

3. The manufacture of claim 1, wherein said first segment comprises a layer, wherein said sanitary napkin has a first face and a second face that is opposite said first face, wherein said first face attaches to said layer and said second face is exposed.

4. The manufacture of claim 1, wherein said sanitary napkin comprises first and second parallel faces separated by a layer, wherein said layer has an exposed side.

5. The manufacture of claim 1, wherein said sanitary napkin comprises first and second parallel faces separated by a layer, wherein said first and second parallel faces join each other at a margin that surrounds said layer, thereby preventing exposure of said layer.

6. The manufacture of claim 1, wherein said strip has a variable width.

7. The manufacture of claim 1, wherein said strip is narrowest at said weakened region and widest within said first and second segments.

8. The manufacture of claim 1, further comprising a cardboard cylinder having an annular cross section, wherein said strip is wound around said cylinder.

9. The manufacture of claim 1, wherein said first sanitary napkin comprises a liquid-absorbing layer that comprises a super-absorbent polymer.

10. The manufacture of claim 1, wherein said first sanitary napkin is die cut.

11. The manufacture of claim 1, wherein said impervious layer is a first impervious layer, wherein each of said sanitary napkins further comprises a second impervious layer, wherein said second impervious layer is attached to said base to form a margin around said first sanitary napkin.

12. The manufacture of claim 1, wherein said weakened region comprises perforations through said strip.

13. The manufacture of claim 1, wherein, at said weakened region, a multiplicity of connecting filaments connect said first and second segments, wherein a sum of widths of said filaments is less than the width of said strip.

14. The manufacture of claim 1, further comprising a webbing that connects said first and second segments to each other at said weakened region.

15. The manufacture of claim 1, wherein said first segment comprises first and second layers, wherein said first sanitary napkin is disposed between said first and second layers, wherein said first and second layers are thermally bonded to each other, and wherein peeling apart said first and second layers enables removal of said first sanitary napkin from said first segment.

16. The manufacture of claim 1, wherein said first segment comprises a layer, wherein said sanitary napkin has a face that is attached to said layer such that peeling off said layer exposes said face, and wherein said layer and said sanitary napkin have a common width.

17. The manufacture of claim 1, wherein said first segment comprises a layer, wherein said sanitary napkin has a face that attached to said layer such that peeling off said layer exposes said face, and wherein said layer includes a message region for having a promotional message imprinted thereon.

18. The manufacture of claim 1, wherein said strip has a central section and margins on either side of said central section, wherein said margins and said central section have the same thickness.

19. The manufacture of claim 1, wherein said strip comprises a central section and margins on either side of said central section, said margins having been folded over to close a gap whose extent depends on a thickness of said central section.

20. The manufacture of claim 1, wherein said strip has a central section and margins on either side of said central section, wherein said margin comprises a first layer and a second layer separated by a gap having a thickness that depends on a thickness of said central section, and wherein said manufacture further comprises a spacer material disposed within said gap.

* * * * *